US012629292B2

(12) United States Patent
Oshima

(10) Patent No.: US 12,629,292 B2
(45) Date of Patent: May 19, 2026

(54) ATTACHABLE-TYPE DISPOSABLE WEARING ARTICLE

(71) Applicant: DAIO PAPER CORPORATION, Shikokuchuo (JP)

(72) Inventor: Aya Oshima, Tochigi (JP)

(73) Assignee: Daio Paper Corporation, Ehime (JP)

( * ) Notice: Subject to any disclaimer, the term of this patent is extended or adjusted under 35 U.S.C. 154(b) by 730 days.

(21) Appl. No.: 17/997,969

(22) PCT Filed: Jun. 3, 2021

(86) PCT No.: PCT/JP2021/021252
§ 371 (c)(1),
(2) Date: Apr. 13, 2023

(87) PCT Pub. No.: WO2021/261206
PCT Pub. Date: Dec. 30, 2021

(65) Prior Publication Data
US 2023/0248586 A1 Aug. 10, 2023

(30) Foreign Application Priority Data
Jun. 23, 2020 (JP) ................................ 2020-108214

(51) Int. Cl.
*A61F 13/15* (2006.01)
*A61F 13/49* (2006.01)
(Continued)

(52) U.S. Cl.
CPC ...... *A61F 13/496* (2013.01); *A61F 13/49001* (2013.01); *A61F 13/49466* (2013.01); *A61F 13/622* (2013.01); *A61F 2013/49084* (2013.01)

(58) Field of Classification Search
CPC .............. A61F 13/496; A61F 13/49001; A61F 13/49466; A61F 13/622; A61F 13/5633; A61F 13/58; A61F 2013/49084
(Continued)

(56) References Cited

U.S. PATENT DOCUMENTS

| 2017/0246055 A1 | 8/2017 | Barnes |
| 2018/0055698 A1* | 3/2018 | Bishop .................. A61F 13/496 |

FOREIGN PATENT DOCUMENTS

| JP | 2010125132 A | 6/2010 |
| JP | 201632591 A | 3/2016 |

(Continued)

OTHER PUBLICATIONS

International Search Report for PCT/JP2021/021252, mailed Aug. 24, 2021.

(Continued)

*Primary Examiner* — Jacqueline F Stephens
(74) *Attorney, Agent, or Firm* — Andrus Intellectual Property Law, LLP

(57) ABSTRACT

The problem is to provide excellent slipping-down preventive property with a simpler structure. This problem is solved by an attachable-type disposable wearing article configured so that, in the natural length state, as the unfixed area contracts, a pair of side areas of the end flap positioned lateral to the unfixed area are obliquely drawn closer as they extend backward, which results in formation of transverse portion extending in the width direction at the back edge of intermediate area located between the pair of side areas, while obliquely backward portions are formed at the back edges of the side areas positioned more backward as they extend laterally, and in the spread state, the back edge of the (Continued)

end flap extends along the width direction over the extent including from one of the obliquely backward portions to the other.

12 Claims, 16 Drawing Sheets

(51) Int. Cl.
  *A61F 13/494*        (2006.01)
  *A61F 13/496*        (2006.01)
  *A61F 13/62*         (2006.01)
(58) Field of Classification Search
  USPC ........................... 604/358.28, 385.3, 385.29
  See application file for complete search history.

(56)                References Cited

FOREIGN PATENT DOCUMENTS

| | | | |
|---|---|---|---|
| JP | 2016067501 | A | 5/2016 |
| JP | 2020000606 | A | 1/2020 |
| JP | 2020089674 | A | 6/2020 |

OTHER PUBLICATIONS

Extended European Search Report for European Patent Application No. 21828342.2, dated Mar. 22, 2024.

* cited by examiner

[FIG.1]
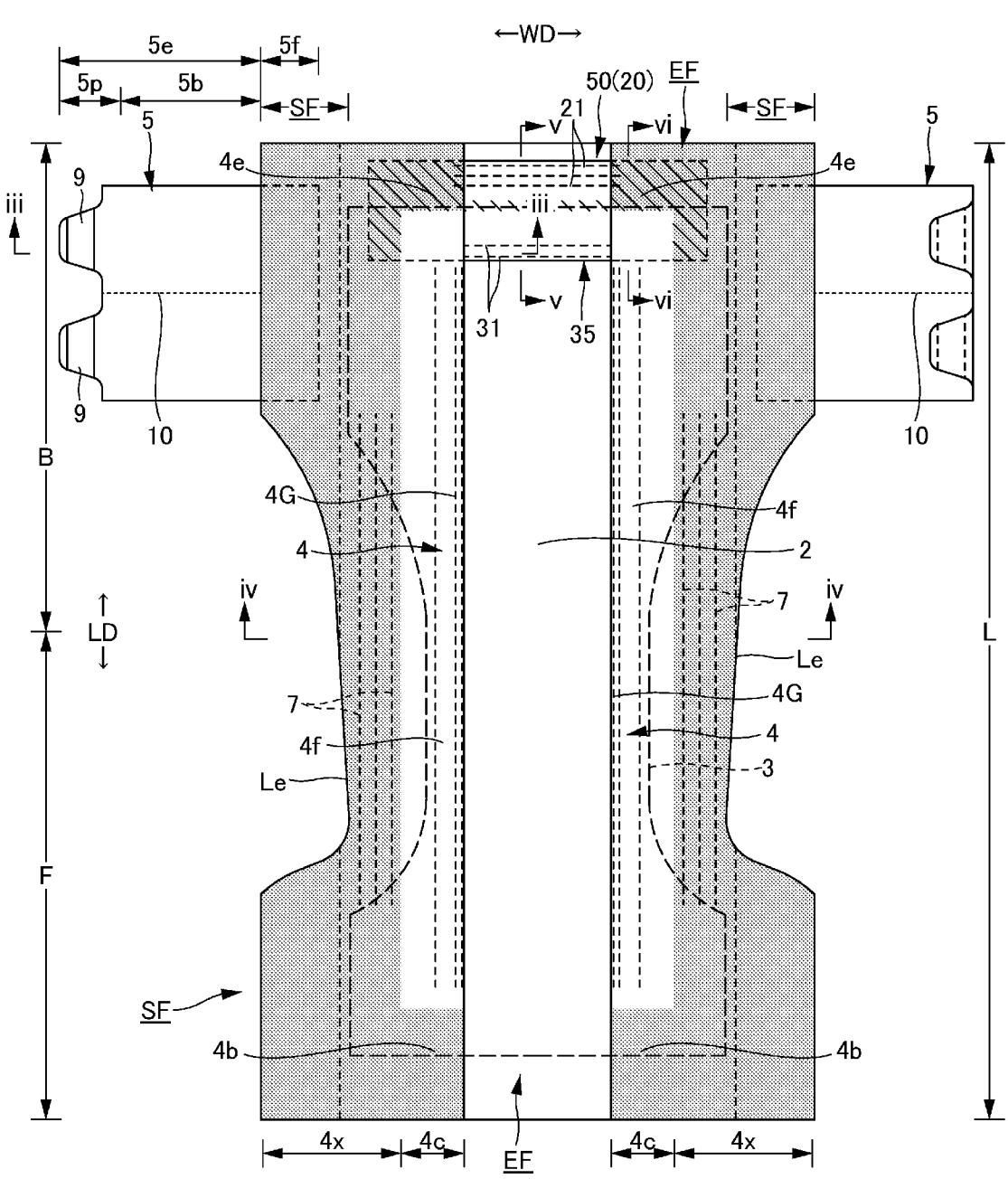

[FIG.2]
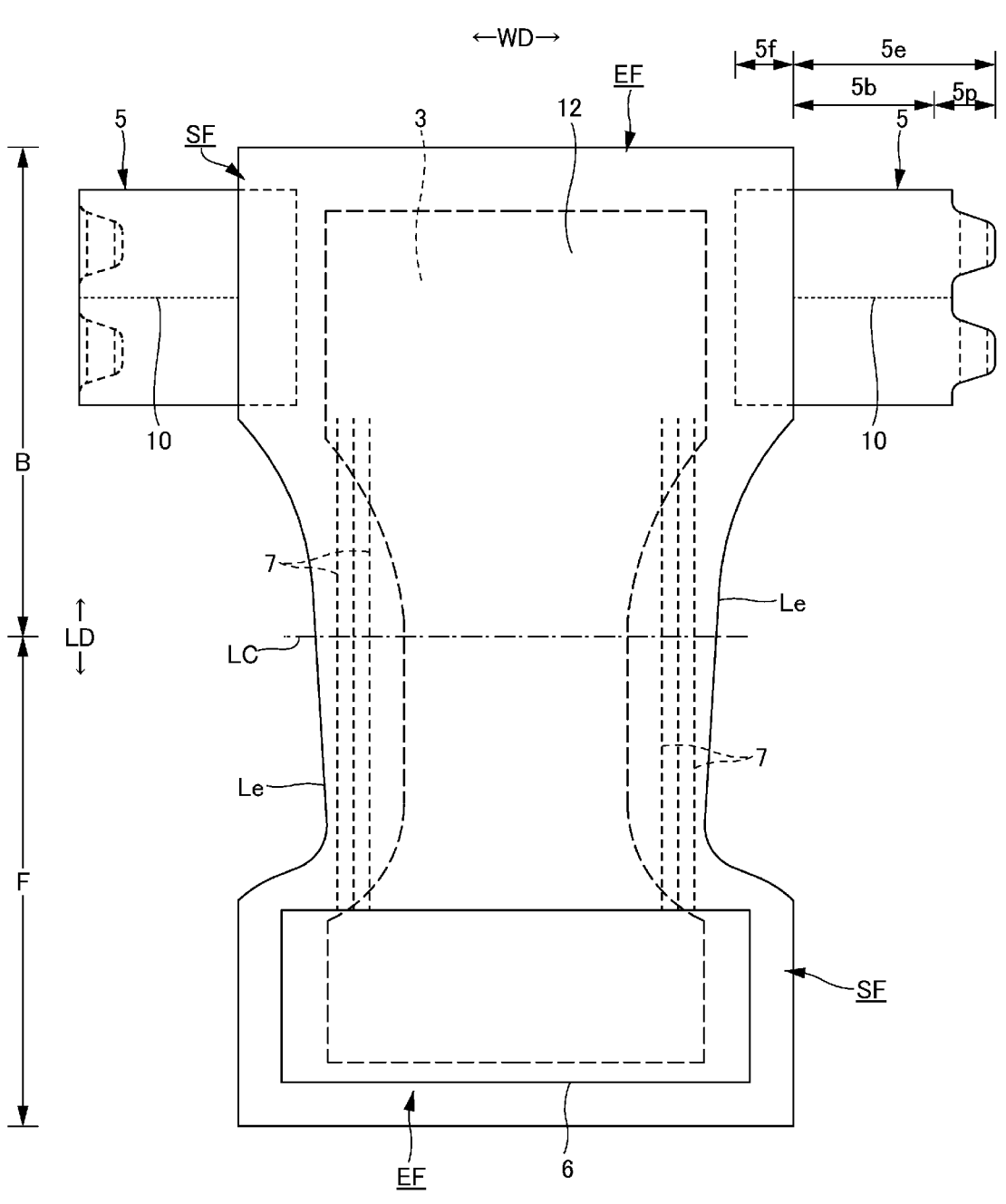

[FIG.3]
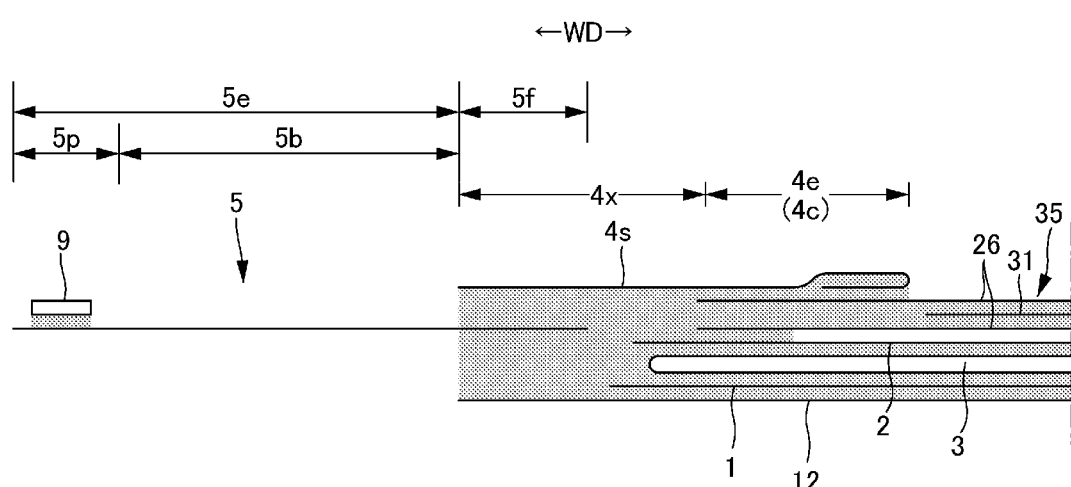

[FIG.4]
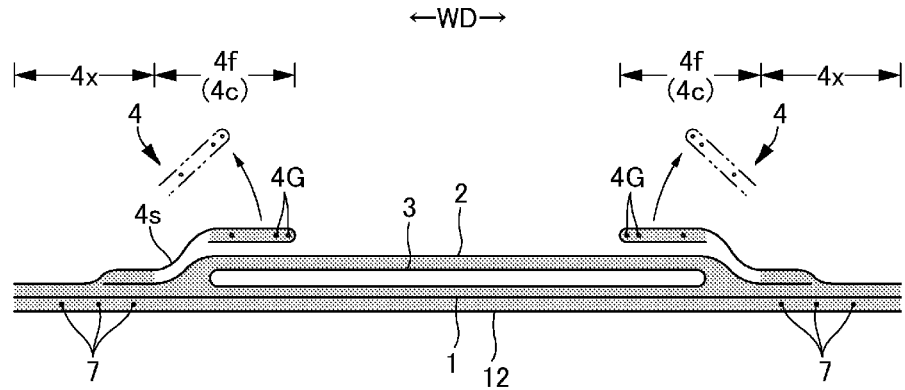

[FIG.5]
(a)
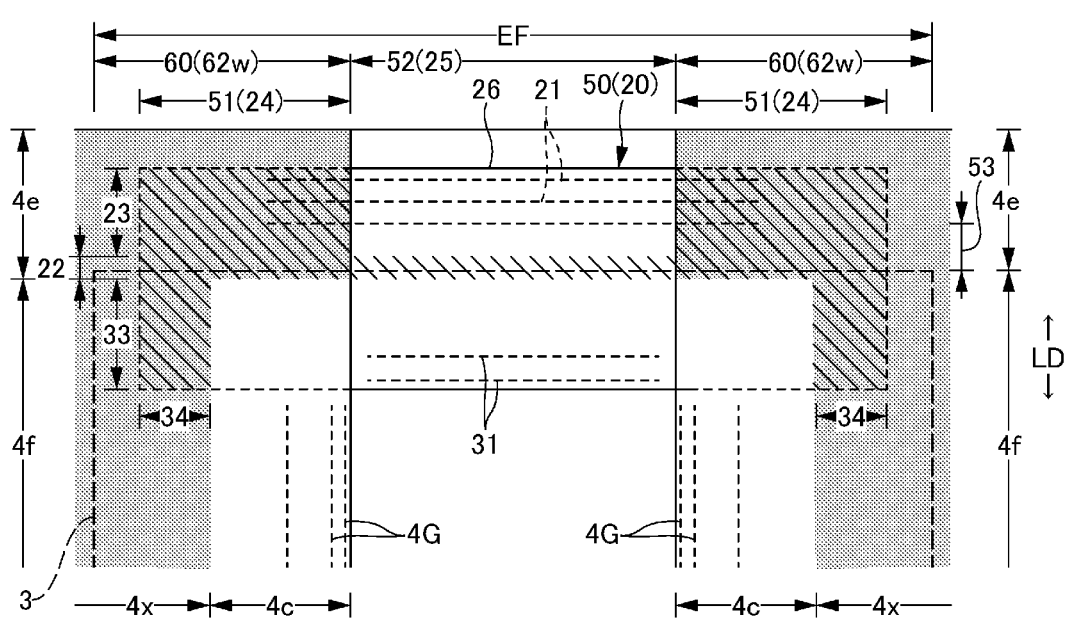
(b)
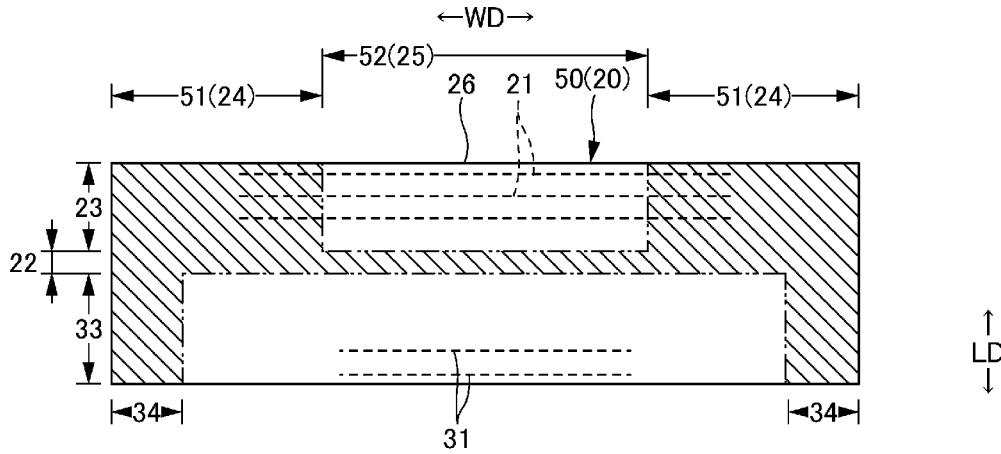

[FIG.6]
(a)
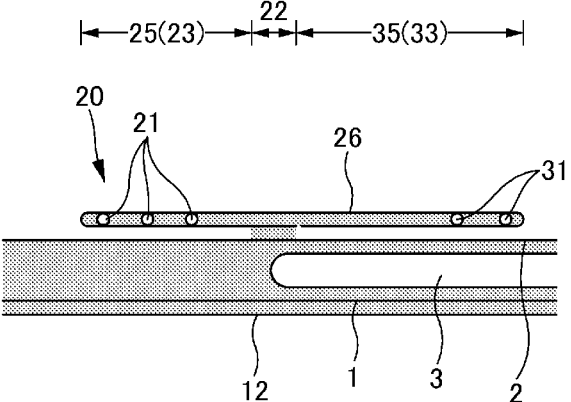
(b)
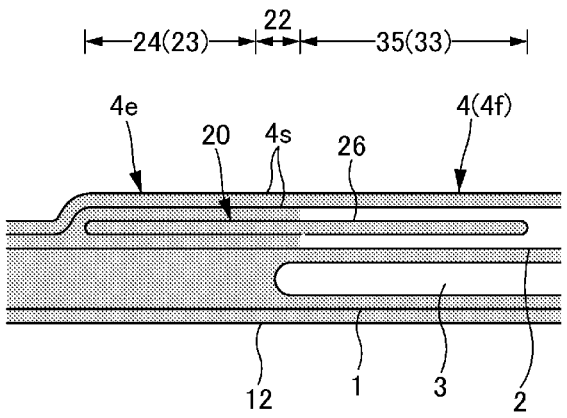

[FIG.7]
(a)
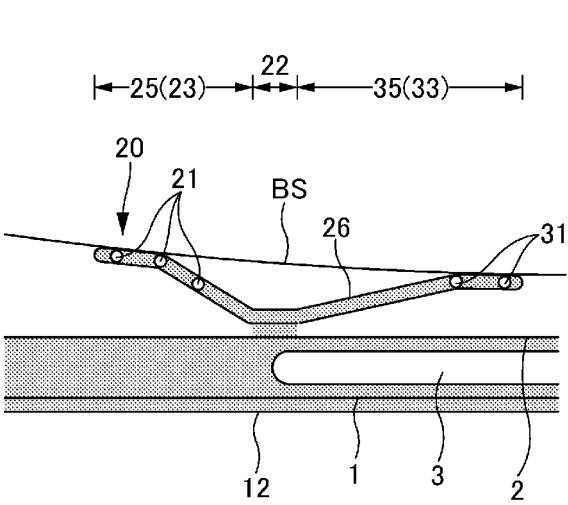
(b)
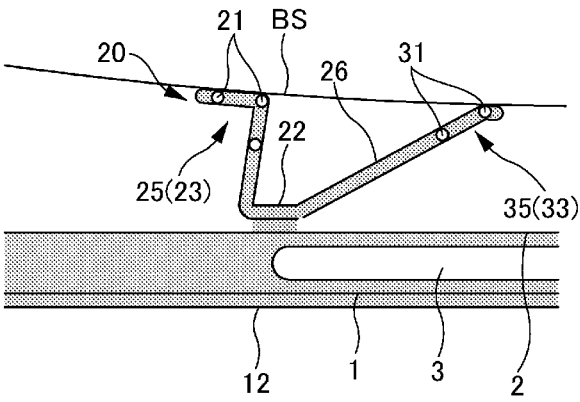

[FIG.8]
(a)
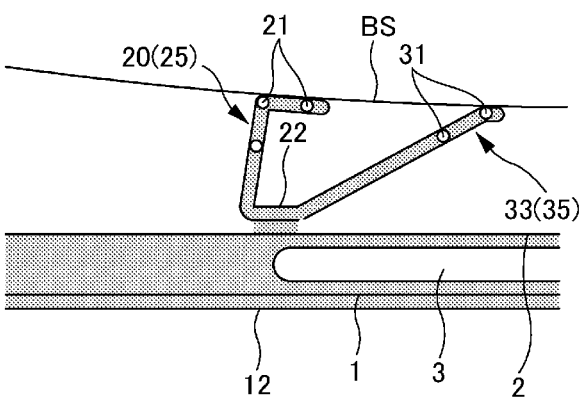
(b)
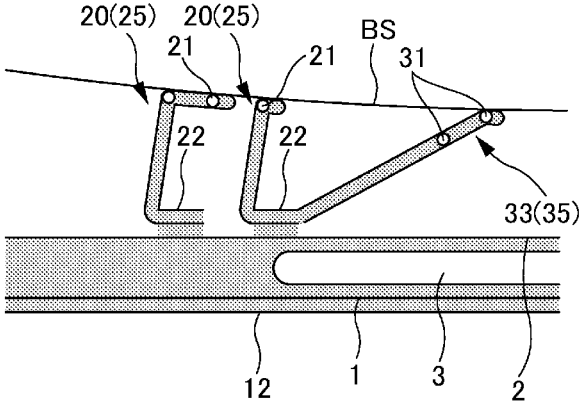

[FIG.9]
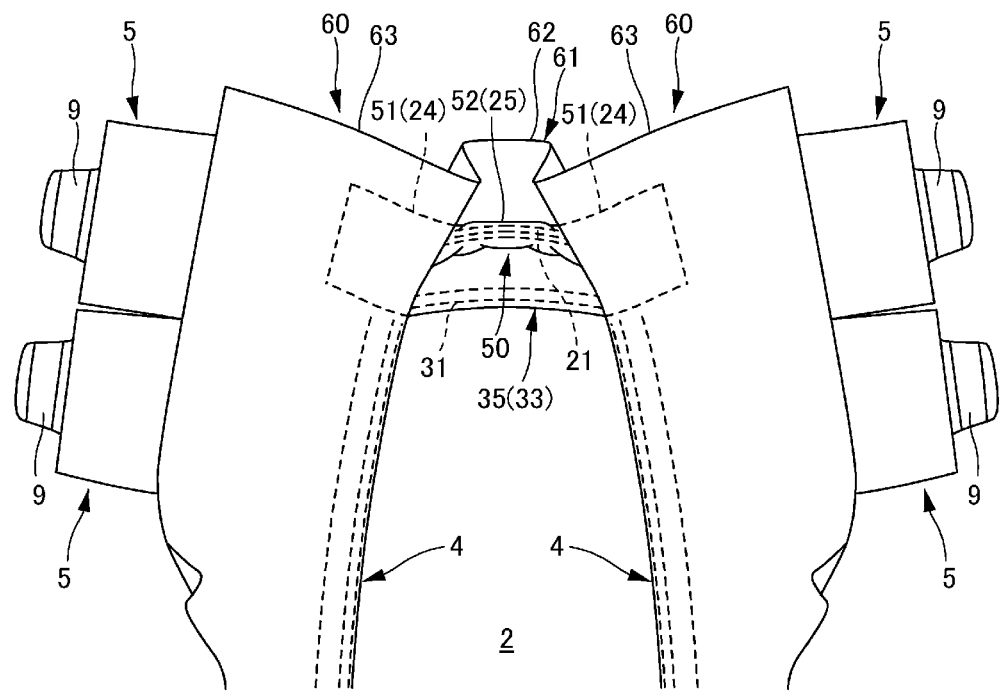

[FIG.10]
(a)
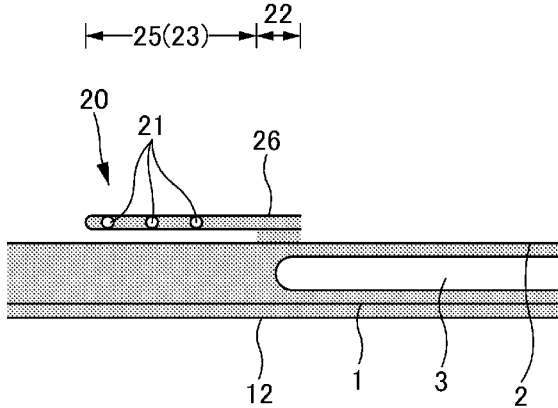
(b)
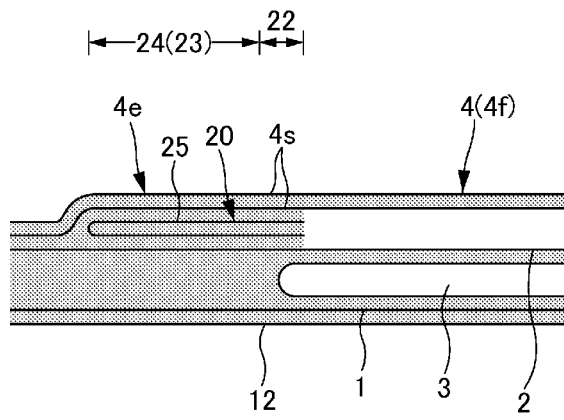

[FIG.11]
(a)
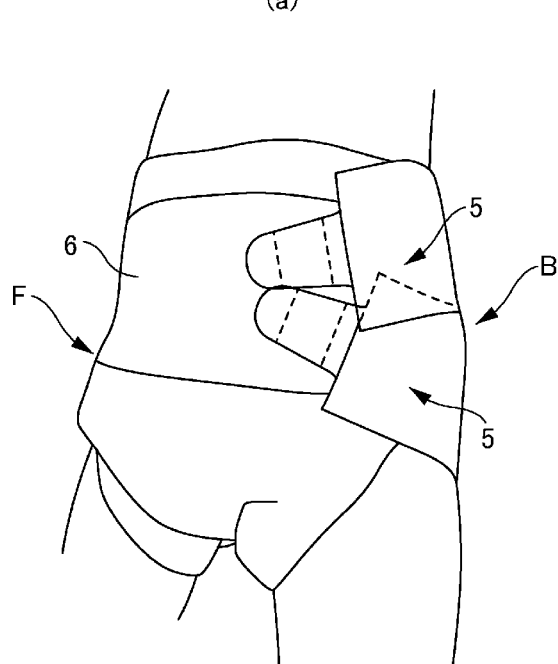
(b)
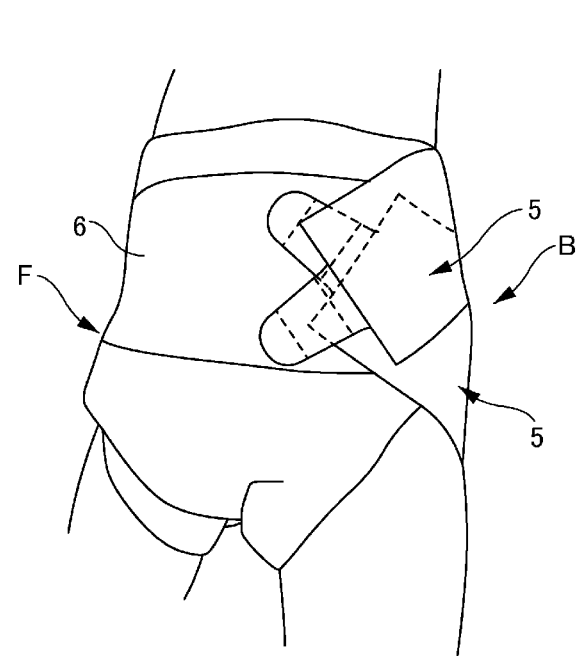

[FIG.12]
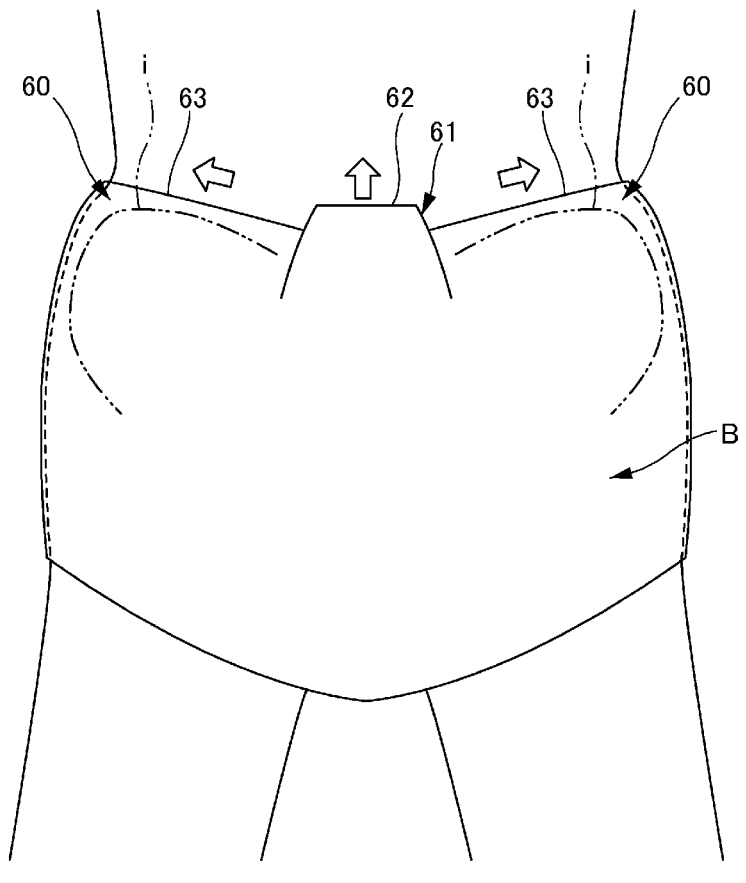

[FIG.13]
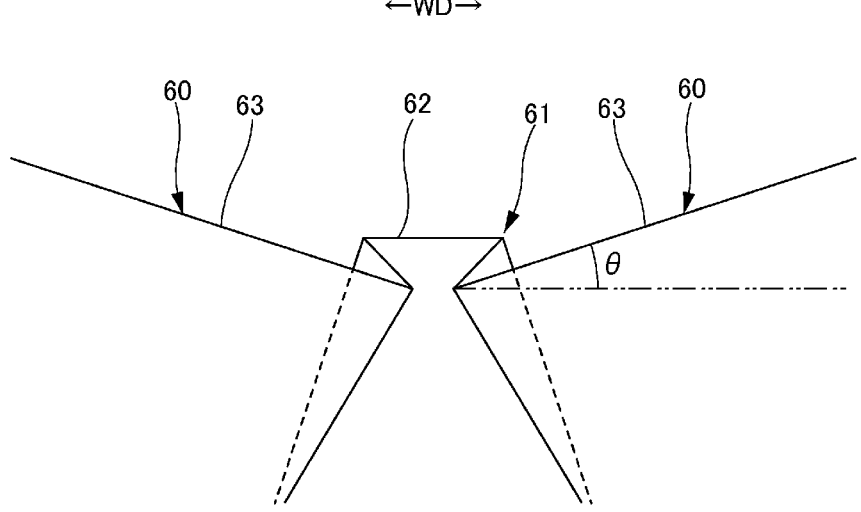

[FIG.14]
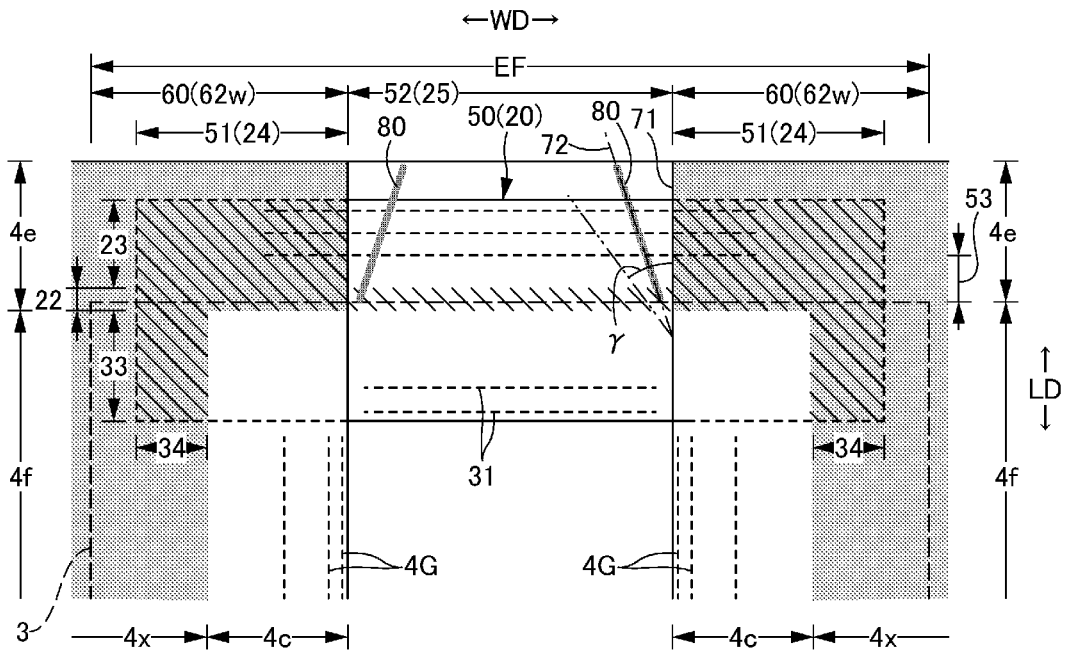

[FIG.15]
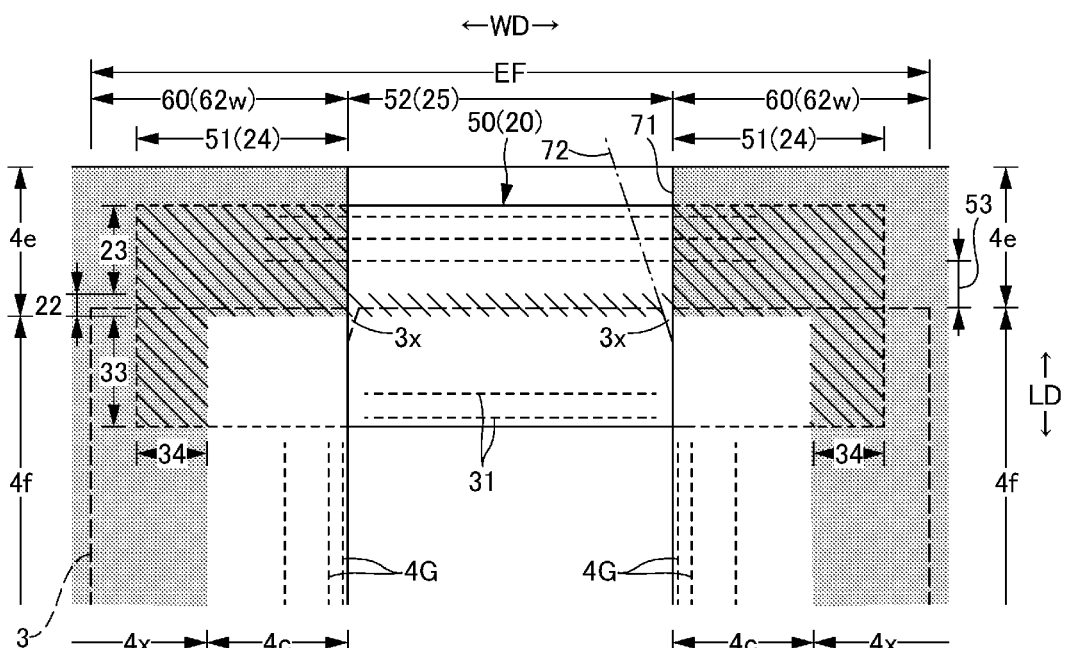

[FIG.16]
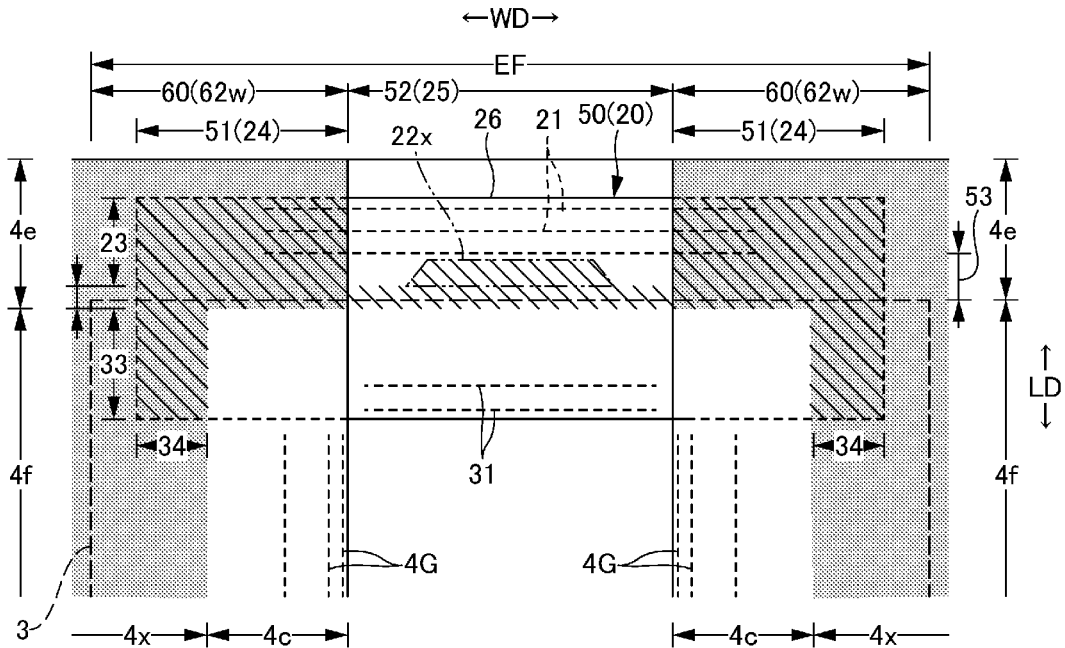

1

ATTACHABLE-TYPE DISPOSABLE WEARING ARTICLE

CROSS-REFERENCE TO RELATED APPLICATIONS

This application is the U.S. national stage application of International Application PCT/JP2021/021252, filed Jun. 3, 2021, which international application was published on Dec. 30, 2021, as International Publication WO 2021/261206 in the Japanese language. The International Application claims priority of Japanese Patent Application No. 2020-108214, filed Jun. 23, 2020. The international application and Japanese application are both incorporated herein by reference, in entirety.

FIELD OF ART

The present invention relates to attachable-type disposable wearing articles.

BACKGROUND ART

A common attachable-type disposable wearing article has a crotch section containing the center of the front-back direction, a ventral section extending forward of the center of the front-back direction, a dorsal section extending backward of the center of the front-back direction, and attaching parts provided in opposed lateral portions of the dorsal section and to be detachably attached to the exterior face of the ventral section. Upon use, the opposed lateral portions of the dorsal section are brought onto the exterior face of the ventral section around the lateral sides of the waist to attach the attaching parts to the exterior face of the ventral section. Such attachable-type disposable wearing articles are not only for use by babies, but also for use in nursing care (adult use) (see, e.g. Patent Literature 1).

In general, attachable-type disposable wearing articles have inferior fitting property in the round-waist direction compared to the underpants-type disposable wearing articles, and are prone to slipping down (liable to be displaced toward the legs). It is thus known that a gap is likely to form between the back of the wearer and the article during use, and leakage is likely to be caused.

One means to solve this problem is to bring the lateral portions opposed in the width direction of the dorsal section around obliquely above the waist onto the exterior face of the ventral section to have the dorsal section caught on the iliac crest.

With many of the conventional attachable-type disposable wearing articles (e.g., those disclosed in Patent Literature 1), however, when the center in the width direction of the back edge of the dorsal section is placed on the waist of a wearer according to the ordinary wearing procedure, the back edge of the dorsal section is located beside the iliac crest, which makes it difficult as it is to have the dorsal section caught on the iliac crest.

In order to solve this problem, it is conceivable to project belts obliquely backward from the opposed lateral portions of the main body section containing the absorber body, to position the free ends of the belts backward of the back edge of the dorsal section in the spread state (see Patent Literature 2). However, this structure is not only complex, but also problematic, as the connecting portions between the wings and the main body section are prone to kink to deteriorate the wearing feeling. In addition, the back edge of the main body section is prone to be located below the waist position (positioned on the crotch side of the waist position of the wearer), and the leak protection effect may be poor irrespective of possible slipping-down preventive effect. Further, the starting ends of the belts oriented obliquely backward are located in the opposed lateral portions of the main body section, and spaced apart to some extent toward the crotch side, which makes it difficult to be caught on the back of the iliac crest.

PRIOR ART LITERATURE

Patent Literature

Patent Literature 1: JP 2010-125132 A
Patent Literature 2: JP 2020-000606 A

SUMMARY OF THE INVENTION

Problems to be Solved by the Invention

It is therefore a primary object of the present invention to provide attachable-type disposable wearing articles having excellent slipping-down preventive property with a simpler structure.

Means for Solving the Problem

The attachable-type disposable wearing articles which achieve the above-mentioned object are as follows:

First Aspect

An attachable-type disposable wearing article having:
a crotch section containing a center of front-back direction, a ventral section extending forward of the center of the front-back direction, and a dorsal section extending backward of the center of the front-back direction,
the attachable-type disposable wearing article including:
attaching parts provided in opposed lateral portions of the dorsal section, and to be detachably attached to an exterior face of the ventral section,
an absorber body disposed in a region including the crotch section,
an end flap exclusive of the absorber body located backward of the absorber body in the dorsal section, and
a deformable stretching/contracting member fixed to the end flap,
the deformable stretching/contracting member having a pair of fixed areas fixed in lateral portions, respectively, opposed in a width direction of the end flap, and an unfixed area elastically stretchable/contractible in the width direction and located between the fixed areas,
wherein the attachable-type disposable wearing article is configured so that, in a natural length state, as the unfixed area contracts, a pair of side areas of the end flap positioned lateral to the unfixed area are obliquely drawn closer to each other as they extend backward, which results in formation of a obliquely backward portions at back edges of the side areas, which extend so as to be positioned more backward as they extend laterally, while transverse portion extends in the width direction at a back edge of an intermediate area located between the pair of side areas are formed which are, and
in a spread state, a back edge of the end flap extends along the width direction over an extent including from one of the obliquely backward portions to the other.

Effect

The present attachable-type disposable wearing article is characterized in that the deformable stretching/contracting member of the particular structure is provided at the particular position, and with the use of its contracting force, the obliquely backward portions which are easily caught on the iliac crest are formed in the dorsal section at the back edge of the side areas in the natural length state (in this state at the beginning of the fitting procedure). In this way, the present attachable-type wearing article provides excellent slipping-down preventive property with an extremely simple structure having the deformable stretching/contracting member. Further, with the deformable stretching/contracting member having the unfixed area, the article is provided with the transverse portion between the obliquely backward portions in the natural length state, so that the positioning of the article against the waist and the iliac crest of the wearer is advantageously facilitated.

Second Aspect

The attachable-type disposable wearing article according to the first aspect,
  wherein the pair of fixed areas is positioned within an extent in the width direction corresponding to an entire width of the absorber body.

Effect

According to the present aspect, the obliquely backward portions are formed from the positions still closer to the center in the width direction, so that the obliquely backward portions are more easily caught on the iliac crest.

Third Aspect

The attachable-type disposable wearing article according to the first or second aspect, further including:
  a pair of first folding lines linearly extending in the front-back direction and each passing a boundary between the unfixed area and one of the fixed areas,
  a pair of second folding lines each extending along a bisector of an internal angle formed by a position of one of the first folding lines in a spread state and a position of the first folding line in a natural length state, wherein a fold is to be made along each second folding line in a direction opposite from a direction in which a fold is to be made along a corresponding first folding line, and
  wherein an easy-fold area is formed along each second folding line.

Effect

In the present attachable-type disposable wearing article, when the pair of side areas in the natural length state are obliquely drawn closer to each other backward as the unfixed area contracts, the intermediate area is readily folded neatly without any superfluous portion, while the transverse portion and the obliquely backward portions are securely formed. As a result, the wearing procedure is facilitated.

Fourth Aspect

The attachable-type disposable wearing article according to any one of the first to third aspects, further including:

a pair of first folding lines linearly extending in the front-back direction and each passing a boundary between the unfixed area and one of the fixed areas,
  a pair of second folding lines each extending along a bisector of an internal angle formed by a position of one of the first folding lines in a spread state and a position of the first folding line in a natural length state, wherein a fold is to be made along each second folding line in a direction opposite from a direction in which a fold is to be made along a corresponding first folding line,
  wherein vertices between the first folding lines and the second folding lines are located forward of a back edge of the absorber body, and
  wherein the absorber body is free of parts each present between one of the first folding lines and a corresponding second folding line in the spread state.

Effect

In order to make the obliquely backward portions more readily caught on the iliac crest, it is preferred that the obliquely backward portions are formed more obliquely and from the positions still closer to the center in the width direction. In this case, however, the vertices between the first folding lines and the second folding lines are located forward of the back edge of the absorber body, whereby the rigidity of the absorber body disturbs the folding along the first folding lines and the second folding lines. Thus, it is preferred, as in the present attachable-type disposable wearing article, that the absorber body is caused to have the lacking parts, so that the rigidity of the absorber body will hardly disturb the folding along the first folding lines and the second folding lines.

Fifth Aspect

The attachable-type disposable wearing article according to any one of the first to fourth aspects,
  wherein a dimension in the width direction of an elastically stretchable/contractible zone in the unfixed area is 10 to 25% an overall length of the article,
  wherein a stretch rate of the unfixed area is 120 to 300%, and
  wherein a distance between the back edge of the absorber body and a front edge of an elastic material contained in the unfixed area is 0 to 10% the overall length of the article.

Effect

The dimensions and positional relationships of various parts may suitably be decided, and are usually preferably within the above-mentioned ranges.

Sixth Aspect

The attachable-type disposable wearing article according to any one of the first to fifth aspects, further including:
  side three-dimensional gather parts standing up from a top face along first shielding positions on lateral sides opposed in the width direction,
  wherein each of the side three-dimensional gather parts has a side root zone fixed outward in the width direction of a first shielding position, and a first zone extending from the side root zone, and includes a first front laid-down portion and a first back laid-down portion formed by fixing front and back end portions, respectively, of the first zone in a laid down state, a first standup portion formed by unfixing the first zone between the first front laid-down portion and the first back laid-down portion, and a first three-dimensional elastic member fixed at least to a free edge area of the first standup portion, wherein the first standup portion in at least its free edge area is contracted in the front-back direction together with the first three-dimensional elastic member and is stretchable in the front-back direction, the attachable-type disposable wearing article further including:

a waist three-dimensional gather part standing up from a top face along a second shielding position between the first back laid-down portions, wherein the waist three-dimensional gather part has a waist root zone fixed along the second shielding position, and a second zone extending from the waist root zone toward back edge, and comprises second laid-down portions formed by fixing lateral end portions opposed in the width direction of the second zone in a laid down state, a second standup portion formed by unfixing a part of the second zone between the second laid-down portions, and a second three-dimensional elastic member fixed at least to a free edge area of the second standup portion, wherein the second standup portion in at least its free edge area is contracted in the width direction together with the second three-dimensional elastic member and is stretchable in the width direction, wherein the deformable stretching/contracting member is the waist three-dimensional gather part, wherein the pair of fixed areas are the second laid-down portions, and wherein the unfixed area is the second standup portion.

Effect

The deformable stretching/contracting member may be a dedicated member, but may preferably act also as the waist three-dimensional gather part as in the present attachable-type disposable wearing article.

That is, the waist three-dimensional gather part of the present article is characterized in that the second standup portion extends toward the waist edge side with respect to the waist root zone, and that the waist three-dimensional gather part is disposed at least one of between the first front laid-down portions and between the first back laid-down portions.

Specifically, in the present waist three-dimensional gather part, as the second standup portion contracts, the second laid-down portions are drawn closer to each other while the second standup portion is raised in its waist edge side toward the crotch section. 0039 On the other hand, in each side three-dimensional gather part, as the first standup portion contracts, the first front laid-down portion and the first back laid-down portion are drawn closer to each other while the first standup portion is raised. Here, the area containing the waist three-dimensional gather part is located at least one of between the first front laid-down portions and between the first back laid-down portions. Accordingly, the action of each side three-dimensional gather part to draw the first front laid-down portion and the first back laid-down portion closer to each other also functions to draw the second zone of the waist three-dimensional gather part closer toward the waist root zone. Further, the area where the direction of contraction of the first standup portions crosses the direction of contraction of the second standup portion, i.e., either the first front laid-down portions or the first back laid-down portions that are provided with the waist three-dimensional gather part, is raised toward the skin of the wearer under the influence of both contractions.

In this way, the second standup portion of the waist three-dimensional gather part is prone to formation of a gap from the skin of the wearer, and its standup state changes characteristically depending on the size of the gap. Specifically, while the gap is smaller, the second standup portion of the waist three-dimensional gather part has its free edge oriented toward the waist edge, has a smaller standup angle, and is in surface contact. That is, at a lower risk for leakage, excellent wearing feeling and fitting is ensured. On the other hand, while the gap is growing, the second standup portion of the waist three-dimensional gather part is raised higher in its free edge area, and is turned over or if not, raised higher up to nearly the turned-over state, toward the crotch side in its free edge area in the middle of the width direction when the constriction around the lower torso is particularly loosened. That is, at a higher risk for leakage, the second standup portion changes its form to provide still more excellent leak protection. Such change in form of the waist three-dimensional gather part has never been proposed to date, and effectively functions against back leakage or front leakage derived from loosening of the article in the worn state over time (e.g., at meal times or the like).

Effect of the Invention

According to the present invention, advantages, such as excellent slipping-down preventive property with a simpler structure, is provided.

BRIEF DESCRIPTION OF THE DRAWINGS

FIG. 1 is a plan view of a tape-type disposable diaper in its spread state, illustrating the interior surface thereof.

FIG. 2 is a plan view of the tape-type disposable diaper in its spread state, illustrating the exterior surface thereof.

FIG. 3 is a cross-sectional view taken along lines iii-iii in FIG. 1.

FIG. 4 is a cross-sectional view taken along lines iv-iv in FIG. 1.

FIG. 5(a) is an enlarged view of a relevant part in FIG. 1, and FIG. 5(b) is an enlarged view of a relevant part of a waist three-dimensional gather part.

FIG. 6(a) is a sectional view taken along lines v-v in FIG. 1, and FIG. 6(b) is a sectional view taken along lines vi-vi in FIG. 1.

FIG. 7 is a sectional view of a relevant part in the worn state.

FIG. 8 is a sectional view of a relevant part in the worn state.

FIG. 9 is a plan view of a tape-type disposable diaper in generally the natural length state before use.

FIG. 10 illustrates sectional views of relevant parts of another embodiment in the spread state.

FIGS. 11(a) and 11(b) are perspective views schematically illustrating worn states of a tape-type disposable diaper.

FIG. 12 is a rear view schematically illustrating a worn state of a tape-type disposable diaper.

FIG. 13 is a plan view of a relevant part of the end flap in its natural length and flattened.

FIG. 14 is an enlarged plan view of a relevant part of another embodiment.

FIG. 15 is an enlarged plan view of a relevant part of another embodiment.

FIG. 16 is an enlarged plan view of a relevant part of another embodiment.

EMBODIMENTS FOR CARRYING OUT THE INVENTION

FIGS. 1 to 6 show a tape-type disposable diaper as an example of attachable-type disposable wearing articles. In the figures, areas bonded with a hot melt adhesive to which reference is necessary for discussion are represented by hatching and dotted pattern in the plan views, and by dotted pattern in the sectional views. The hot melt adhesive may be applied using a known technique, such as slot application, bead application in continuous lines or dotted lines, spray application in spiral or Z shapes, or pattern coating (transfer of a hot melt adhesive by relief printing). In place of or in addition to these, fixing portions of elastic members may be fixed to adjacent members by application of a hot melt adhesive to the external surface of the elastic members. Examples of the hot melt adhesive include, but not limited to, EVA-based, pressure-sensitive rubber-based (elastomer-based), polyolefin-based, and polyester/polyamide-based adhesives. Joining means for joining various components may alternatively be material melt-bonding, such as heat sealing or ultrasonic sealing.

This tape-type disposable diaper has a crotch section containing the center LC of the front-back direction LD, a ventral section F extending forward of the center LC of the front-back direction LD, and a dorsal section B extending backward of the center LC of the front-back direction LD, and includes attaching parts 9 provided in opposed lateral portions of the dorsal section B and to be detachably attached to the exterior face of the ventral section F. Further, this tape-type disposable diaper has an absorber body 3 contained in a region including the crotch section, a liquid-pervious top sheet 2 covering the top side of the absorber body 3, a liquid-impervious sheet 1 covering the underside of the absorber body 3, and an exterior nonwoven sheet 12 covering the underside of the liquid-impervious sheet 1 to constitute the product exterior face.

Materials and features of each part will now be explained in turn.

<Absorber Body>

The absorber body 3 has a basic structure with one or a plurality of layers of an accumulated body of pulp fibers, an assembly of filaments, such as of cellulose acetate, or an assembly layer of fibers formed of nonwoven fabric. The absorber body 3 may have high-absorbent polymers such as in particulate form mixed in the assembly layer of fibers, fixed in or to the surface of the assembly layer of fibers, or interposed in layers between the assembly layer of fibers, where necessary. The absorber body 3 may be wrapped with a packing sheet (not shown) such as of crepe paper, where necessary. The shape of the absorber body 3 may suitably be decided, and may preferably be an hourglass-like shape (narrowed shape) having a middle portion in the front-back direction LD including the crotch section narrowed compared to the portions forward and backward thereof as in the illustrate embodiment, or a shape extending from forward of the crotch section to backward thereof, such as a rectangular shape. The fiber basis weight of the absorber body 3 may be about 100 to 500 g/m$^2$, and the thickness thereof may be about 1 to 15 mm. Further, the basis weight of the high-absorbent polymer in the absorber body 3 may be 0 to about 300 g/m$^2$.

<Liquid-Impervious Sheet>

The liquid-impervious sheet 1 blocks seeping of bodily waste out to the underside. The liquid-impervious sheet 1 may be formed of a plastic film, such as polyethylene film, or a sheet imparted with moisture permeability without impairing water shielding property for preventing dampness. Such a water-shielding, moisture-permeable sheet may be a microporous sheet obtained by kneading an inorganic filler in a polyolefin-based resin, such as polyethylene or polypropylene, in a molten state, forming the resulting mixture into a sheet, and then uni- or biaxially drawing the sheet.

The liquid-impervious sheet 1 preferably extends coincident with or to the wider extent than the absorber body 3 in the front-back direction LD and in the width direction WD but, in the presence of another water-shielding means, may be arranged so as not to cover the ends and edges in the front-back direction LD and the width direction WD of the absorber body 3, as required.

In order to impart fabric-like appearance and texture to the exterior of the diaper, the entire underside of the liquid-impervious sheet may be covered with an exterior nonwoven sheet 12. The exterior nonwoven sheet 12 may be omitted, in which case the liquid-impervious sheet 1 constitutes the product exterior.

<Top Sheet>

The top sheet 2 is liquid-pervious, and may be, for example, perforated or imperforated nonwoven fabric or porous plastic sheet.

The top sheet 2 extends in the front-back direction LD from the front end to the back end of the product, and in the width direction WD laterally beyond the absorber body 3, but its shape may suitably be modified, for example, so that the width of the top sheet 2 is shorter than the entire width of the absorber body 3, where, for example, the starting points of side three-dimensional gather parts 4 to be discussed later are located on the center side in the width direction WD of the side edges of the absorber body 3, or otherwise required.

<Side Flaps>

The tape-type disposable diaper of the illustrated embodiment has a pair of side flaps SF exclusive of the absorber body 3, extending respectively laterally beyond the opposed lateral edges of the absorber body 3. The side flaps SF may be formed of the material continuous from the region containing the absorber body 3 (exterior nonwoven sheet 12 or the like), or may be formed of another material and attached.

<Planar Gathers>

In the middle portion in the front-back direction LD of each side flap SF, elongate round-leg elastic members 7 are fixed in their stretched state in the front-back direction LD between the liquid-impervious sheet 1 and the exterior nonwoven sheet 12, with a hot melt adhesive or the like. By the contraction of the round-leg elastic members 7, so-called planar gathers are formed in the side flaps. Such planar gathers allow the diaper to elastically contract and stretch in their lateral portions to fit around the legs. The round-leg elastic members 7 may be curved around the legs.

The number of the round-leg elastic members 7 on each of the right and left sides may suitably be decided, and about one to ten, more preferably about three to eight of them are suitably used. A plurality of them, if used, may preferably be arranged at about 2 to 15 mm intervals, particularly about 6 to 10 mm intervals. Further, each round-leg elastic member 7 may be made of a material that is usually used, for example, polystyrene rubber, polyolefin rubber, polyurethane rubber, polyester rubber, polyurethane, polyethylene, polystyrene, styrene-butadiene, silicone, or polyester, and formed into, for example, a thread, string, or tape shape. The fineness of the round-leg elastic members may preferably be about 500 to 1500 dtex, and about 0.1 to 3 mm, in particular about 0.5 to 3 mm for natural rubber. The stretch rate of each round-leg elastic member 7 in the fixed state may preferably be about 150 to 250%.

<Wings>

In the present tape-type disposable diaper, the dorsal section B is provided with wings extending beyond the crotch section M in the width direction WD. Similarly, the ventral section F is also provided with wings extending beyond the crotch section M in the width direction WD. These wings may be formed of parts separate from the remaining portions. However, in the structure having the side flaps SF as in the illustrated embodiment, it is preferred for facilitating production that the wings are formed by cutting out each lateral side of the side flap SF in the middle in the front-back direction LD to form a concave round-leg edge Le extending from the lateral edge of the crotch section to the lower edge of each wing.

<Attaching Tapes>

The dorsal section B has, in its opposed lateral portions (on the wings in the side flaps SF in the illustrated embodiment), attaching tapes 5 attached thereto and projecting beyond the respective side edges, whereas the ventral section F has, on its surface in the lower torso portion, a target sheet 6 adhered thereto in the width direction WD. In wearing the diaper on the user body, with the diaper 100 placed on the body, the attaching tapes 5 on the opposed lateral sides are brought around the lateral sides of the waist onto the exterior face of the ventral section to engage the target sheet 6. Alternatively, the target sheet 6 may be omitted, in which case, the attaching tapes 5 directly engage the exterior face of the diaper (the exterior nonwoven sheet 12 in the illustrated embodiment).

As shown in FIG. 3, each attaching tape 5 has a fixed portion 5f fixed between the sheets in the side flap SF in the dorsal section B, with means, such as a hot melt adhesive, and a projecting portion 5e projecting from between the sheets at the side edge of the side flap SF outward in the width direction WD, wherein the projecting portion 5e has a distal area 5p and a main body area 5b proximal to the distal area 5p. On the inner face of the distal area 5p of each attaching tape 5, hook member of a mechanical fastener (male member of a hook and loop fastener) is fixed, which has a number of hook-shaped projections on its surface, as an attaching part 9 for attachment to the target sheet 6. As a target sheet 6, a member having a surface on which the hook-shaped projections detachably engages (female member of a mechanical fastener (hook and loop fastener)) is attached to the exterior face of the ventral section F. The material per se constituting the exterior face of the diaper may be used in place of the target sheet 6, or a pressure-sensitive adhesive layer may be used as the attaching part 9 in place of the hook member while a resin tape having a smooth surface for good pressure-sensitive adhesion may be used as the target sheet 6.

Further, as shown in FIG. 1, each attaching tape 5 is provided with a perforated line 10 extending in the middle of the front-back direction LD along the width direction WD from the outer edge in the width direction WD into the main body area 5b, and by tearing this perforated line 10, each attaching tape 5 may be separated into an upper segment and a lower segment, each having the fixing portion, the main body area, the distal area, and the attaching part 9, as shown in FIG. 9. The attaching tape 5 may be separated into the upper and lower segments in advance by cutting or the like means, instead of the perforated line 10. Such an attaching tape 5 may be attached detachably to the target sheet 6 in the ventral section F with the upper segment oriented obliquely downward and the lower segment oriented obliquely upward without crossing with each other as shown in FIG. 11(*a*), or with the upper and lower segments crossed as shown in FIG. 11(*b*).

It is indisputable that, in the present attachable-type disposable wearing articles, the attaching tapes are not limited to those divided into the upper and lower segments but may alternatively be those not divided into two segments, those having only one segment, or any other commonly known attaching tapes, or the attaching parts may directly be fixed to the side flaps.

<Side Three-Dimensional Gather Parts>

As shown in FIGS. 1, 4, and 6, in order to block the bodily waste migrating in the width direction on the top sheet 2 to thereby prevent so-called side leakage, on the lateral sides opposed in the width direction of the top face are provided side three-dimensional gather parts 4 standing up from the top face along the first shielding positions extending in the front-back direction.

More specifically, each of the side three-dimensional gather parts 4 has a side root zone 4x fixed to the region including the side flap SF, a first zone 4c extending from the side root zone 4x, a first front laid-down portion 4b and a first back laid-down portion 4e formed by fixing the front and back end portions, respectively, of the first zone 4c in a laid down state, and a first standup portion 4f formed by unfixing the first zone 4c between the first front laid-down portion 4b and the first back laid-down portion 4e. The first standup portion 4f has first three-dimensional elastic members 4G fixed at least in its free edge area.

Each of the side three-dimensional gather parts 4 in the illustrated embodiment is formed of a side three-dimensional sheet 4s, which is folded in double to form the free edge of the first zone 4c (the edge opposite from the root portion 65), so that the area including the free portion has a double-layered structure. The first three-dimensional elastic members 4G are interposed between the layers of this double-layered structure. The first three-dimensional elastic members 4G may be provided only in the standup portion 4f, or may preferably be fixed, as in the illustrated embodiment, from the back end area of the first front laid-down portion 4b over to the front end area of the first back laid-down portion 4e, so that the contracting force of the first three-dimensional elastic members 4G acts not only over the entire standup portion 4f, but also on the end areas of the first front laid-down portion 4b and the first back laid-down portion 4e.

The inner face of each side three-dimensional sheet 4s has a joining start edge in the width direction WD positioned in the lateral portion of the top sheet 2, and the area outward in the width direction WD of this joining start edge is bonded with a hot melt adhesive or the like to the inner face of the corresponding side flap SF, i.e., in the illustrated embodiment, to the lateral portion of the liquid-impervious sheet 11 and to the lateral portion of the exterior nonwoven sheet 12 located laterally outward thereof in the width direction WD. In the plan views, the dotted pattern represents the fixed area of the side three-dimensional gather parts 4.

The area of each side three-dimensional gather part 4 inward in the width direction WD of the joining start edge is fixed to the top sheet 2 in the end portions opposed in the front-back direction, while the first standup portion 4f between the end portions of the side three-dimensional gather part 4 is an unfixed free portion. Accordingly, under the contracting force of the first three-dimensional elastic members 4G, the first standup portion 4*f* is contracted in the front-back direction and raised while it is stretchable in the front-back direction, resulting in close contact with the body surface. Further, the first standup portion 4*f*, while contracting in the front-back direction under the contracting force of the first three-dimensional elastic members 4G, deforms to draw the first front laid-down portion 4*b* and the first back laid-down portion 4*e* closer to each other.

Though not shown, as is well known, the first zone 4*c* of each side three-dimensional gather part 4 may be formed in double, having a proximal portion extending from laterally outer side to laterally inner side in the width direction WD, and a distal portion folded toward the body and extending laterally outward in the width direction WD from the edge of the proximal portion located closer to the center of the width WD, and such a first zone 4*c* may be fixed in the end portions opposed in the front-back direction LD to form laid-down portions.

The side three-dimensional sheets 4*s* are not particularly limited in type, and are usually water-repelling for ensuring liquid-shielding property. In particular, for imparting both texture and liquid-shielding property, nonwoven fabric having at least one melt-blown layer between spunbonded layers (SMS nonwoven fabric, SMMS nonwoven fabric, SSMS nonwoven fabric, or SSMMS nonwoven fabric) is preferred. One sheet of nonwoven fabric may be used, or a plurality of sheets of nonwoven fabric may be stacked and used. In the latter case, the nonwoven sheets may preferably be adhered together with a hot melt adhesive or the like.

Each first three-dimensional elastic member 4G may be made of a material that is usually used, for example, natural rubber or synthetic rubber formed into, for example, a thread, string, or tape shape, specifically, polystyrene rubber, polyolefin rubber, polyurethane rubber, polyester rubber, polyurethane, polyethylene, polystyrene, styrene-butadiene copolymer, silicone, or polyester. A plurality of the first three-dimensional elastic members 4G may be arranged at intervals as shown in FIGS. 1 and 2, or only one of them may be disposed. The stretch rate of the first three-dimensional elastic members 4G in the spread state may suitably be decided, and may be, for example, about 230 to 270% in the case of spandex rubber threads having a fineness of about 420 to 1120 dtex.

<End Flaps>

The present tape-type disposable diaper has a pair of end flaps EF exclusive of the absorber body 3, extending respectively on the front and back sides of the absorber body 3. The materials constituting the end flaps EF may vary depending on the structure of the diaper. In the illustrated embodiment, each end flap EF may be formed from portions of the liquid-impervious sheet 1, the exterior nonwoven fabric sheet 12, the top sheet 2, and the side three-dimensional sheet 4*s* which extend forward and backward of the absorber body 3, are stacked on one another, and are joined together, but are not limited thereto. A separate sheet for forming an end flap EF may be fixedly joined on the front or back of the absorber body 3 to form an end flap EF.

Usually, the front-back LD dimension of each end flap EF may be about 1 to 10% the front-back LD dimension of the overall diaper.

<Deformable Stretching/Contracting Member and Waist Three-Dimensional Gather Part>

On the other hand, in the back end portion of the disposable diaper (end flap EF in the illustrated embodiment) according to the embodiment illustrated in FIGS. 1, 5, and

6, a waist three-dimensional gather part 20 also acting as a deformable stretching/contracting member 50 is provided. That is, an end flap EF is provided with a waist three-dimensional gather part 20 standing up from the top face along a second shielding position between the first back laid-down portions 4*e*. Specifically, as shown in FIGS. 5 and 6, the waist three-dimensional gather part 20 has a waist root zone 22 fixed to the end flap EF along the second shielding position, and a second zone 23 extending from the waist root zone 22 toward the waist edge, second laid-down portions 24 (fixed areas 51) formed by fixing the lateral end portions opposed in the width direction WD of the second zone 23 in a laid down state, and a second standup portion 25 (unfixed area 52) formed by unfixing a part of the second zone 23 between the second laid-down portions 24. Further, the second standup portion 25 has second three-dimensional elastic members 21 fixed at least to its free edge area (end portion on the waist edge side) for elastic stretching and contraction in the width direction WD.

In the natural length state, as shown in FIG. 9, a pair of side areas 60 of the end flap EF positioned lateral to the second standup portion 25 are obliquely drawn closer to each other as they extend backward, by the contraction of the second standup portion 25 under the interference of contraction by the high rigidity region including the absorber body 3, whereby obliquely backward portions 63 are formed at the back edges of the side areas 60, which are positioned more backward as they extend laterally, while a transverse portion 62 extends in the width direction WD at the back edge of an intermediate area 61 located between the pair of side areas 60. In other words, the obliquely backward portions 63 extend backward beyond the transverse portion 62. Further, in the spread state, as shown in FIGS. 1 and 5, the back edge of the end flap EF extends over the range including from one of the obliquely backward portions 63 to the other, and in a suitable form, such as linearly, along the width direction WD.

Thus, in the present disposable diaper, the obliquely backward portions 63 are formed at the back edge of the dorsal section B in the side areas 60 in the natural length state (in this state at the beginning of the wearing procedure) as shown in FIG. 9, so that these obliquely backward portions 63 are readily caught on the iliac crest i as shown in FIG. 12. Further, the presence of the unfixed area 52 in the deformable stretching/contracting member 50 provides the transverse portion 62 between the obliquely backward portions 63 in the natural length state, which facilitates the positioning of the diaper with respect to the waist and the iliac crest i of the wearer.

The angle with respect to the width direction WD and the dimension in the width direction WD of each obliquely backward portion 63 may suitably be decided and, in a state where the obliquely backward portions 63 are pressed with a flat transparent plate placed thereon (see FIG. 13), the angle θ of each obliquely backward portion 63 with respect to the width direction WD may preferably be about 5 to 20 degrees, and the dimension 62*w* in the width direction WD of each obliquely backward portion 63 (see FIG. 5) may preferably be about 10 to 15% the overall length L of the article.

For imparting such angle and dimension, the dimensions and positional relationships of various parts may suitably be decided and, usually, the dimension in the width direction WD of an elastically stretchable and contractible zone in the second standup portion 25 (in the illustrate embodiment, the zone of the second standup portion 25 containing the second three-dimensional elastic members 21) is preferably 10 to 25% the overall length L of the article. The stretch rate of the second standup portion 25 is preferably 120 to 300%. Further, the distance 53 between the back edge of the absorber body 3 and the front edge of the second three-dimensional elastic members 21 (elastic material) (where a plurality of second three-dimensional elastic members 21 are disposed, the distance between the back edge of the absorber body 3 and the front edge of the front-most elastic member) is preferably 0 to 10% the overall length of the article.

The pair of fixed areas 51 of the deformable stretching/contracting member 50 may be positioned outside the extent in the width direction WD corresponding to the entire width of the absorber body 3. However, with the second laid-down portions 24 positioned within the extent in the width direction WD corresponding to the entire width of the absorber body 3 as in the illustrated embodiment, the obliquely backward portions 63 may be formed from the positions still closer to the center in the width direction WD, to be more readily caught on the iliac crest i, which is preferable.

In the present disposable diaper, it is preferable, in the natural length state, that the intermediate area 61 is folded to have a Z-shaped cross-section as shown in FIGS. 9 and 13, when the pair of side areas 60 are obliquely drawn closer to each other as they extend backward by the contraction of the unfixed area 52, but if the intermediate area 61 is not folded neatly without any superfluous portion, unnecessary creases may deteriorate the wearing feeling and appearance. In view of this, as shown in FIG. 14, it is preferred to provide a pair of first folding lines 71 linearly extending in the front-back direction LD and each passing the boundary between the unfixed area 52 and one of the fixed areas 51, a pair of second folding lines 72 each extending along the bisector of the internal angle γ formed by the position of one of the first folding line 71 in the spread state and the position of the first folding line 71 in the natural length state and in the flatly pressed state (shown in chain double-dashed line in the figures), wherein a fold is to be made along each second folding line 72 in the direction opposite from the direction in which a fold is to be made along the corresponding first folding line 71, and an easy-fold area 80 formed along each second folding line 72. The easy-fold areas 80 are not particularly limited as long as a fold may be made more easily in this area than in the remaining area, and may be formed by embossing, formation of a perforated line 10, or creasing, or by melting and solidifying a material, such as heat sealing or ultrasonic sealing. In this way, the intermediate area 61 may be made to be easily folded neatly without any superfluous portion, so that the transverse portion 62 and the obliquely backward portions 63 are securely formed. As a result, the wearing procedure of the article may be facilitated.

In the present disposable diaper, in order to make the obliquely backward portions 63 more readily caught on the iliac crest i, it is preferred that the obliquely backward portions 63 are formed more obliquely and from the positions still closer to the center in the width direction WD. In this case, however, the vertices between the first folding lines 71 and the second folding lines 72 are located forward of the back edge of the absorber body 3, whereby the rigidity of the absorber body 3 disturbs the folding along the first folding lines 71 and the second folding lines 72. In view of this, it is preferred not only that the vertices between the first folding lines 71 and the second folding lines 72 are located forward of the back edge of the absorber body 3, but also that the absorber body 3 does not contain the areas 3x between the first folding lines 71 and the second folding lines 72 in the spread state, as shown in FIG. 15. In this way, by causing the absorber body 3 to have lacking parts 3x, the rigidity of the absorber body 3 will hardly disturb the folding along the first folding lines 71 and the second folding lines 72. In this case, it is preferred to provide the easy-fold areas 80, which, alternatively, may not be provided.

Further, as shown in FIG. 16, the waist root zone 22 may preferably be made, entirely or partially, to project or bulge (area 22x enclosed with the chain double-dashed lines in the figure) so as to be located more backward with increasing proximity to the center of the width WD, which facilitates slanting of the obliquely backward portions 63.

Further detailed discussion will now be made regarding the structure or the like of the waist three-dimensional gather part 20 in the illustrated embodiment. The waist three-dimensional gather part 20 in the illustrated embodiment is formed of waist three-dimensional sheet 26, which is folded to provide the waist three-dimensional gather part 20 with a two-layered structure. Second three-dimensional elastic members 21 are interposed between the layers of this two-layered structure, and fixed therein with a hot melt adhesive or the like. The second three-dimensional elastic members 21 may be provided only in the second standup portion 25, or may preferably be fixed from one of the second laid-down portions 24 over to the other as in the illustrated embodiment, so that the contracting force of the second three-dimensional elastic members 21 acts not only over the second standup portion 25, but also up to the second laid-down portions 24.

The inner face of the waist three-dimensional sheet 26 in the illustrated embodiment has a joining start edge in the front-back direction LD in the end flap EF, and the area backward of this joining start edge is bonded with a hot melt adhesive or the like to the inner face of the end flap EF, i.e., in the illustrated embodiment, to the top face of the top sheet 2. Note that the area of the waist three-dimensional sheet 26 fixed to the top sheet 2 is indicated by hatching with negative slope in FIGS. 1 and 5(a).

On the waist edge side of the joining start edge, the waist three-dimensional gather part 20 has, in its lateral portions opposed in the width direction WD, the second laid-down portions 24 fixed to the top sheet 2, and the second standup portion 25 located therebetween, which is an unfixed free portion. Accordingly, under the contracting force of the second three-dimensional elastic members 21, the second standup portion 25 is contracted in the width direction WD and raised while it is stretchable in the width direction WD, resulting in close contact with the body surface. Further, the second standup portion 25, while contracting in the width direction WD under the contracting force of the second three-dimensional elastic members 21, deforms to draw the area containing one of the second laid-down portions 24 and the area containing the other closer to each other.

On the other hand, in each side three-dimensional gather part 4, as the first standup portion 4f contracts, the first front laid-down portion 4b and the first back laid-down portion 4e are drawn closer to each other while the first standup portion 4f is raised. Here, the area containing the waist three-dimensional gather part 20 is located between the first back laid-down portions 4e. Accordingly, the action of the side three-dimensional gather parts 4 to draw the first front laid-down portions 4b and the first back laid-down portions 4e closer to each other (see the arrows in FIG. 9) also functions to draw the second zone 23 of the waist three-dimensional gather part 20 closer toward the waist root zone 22 (see the arrows in FIG. 9). Further, the area where the direction of contraction of the first standup portions 4f crosses the direction of contraction of the second standup portion 25, i.e., either the first front laid-down portions 4b or the first back laid-down portions 4e that are provided with the waist three-dimensional gather part 20, is raised toward the skin of the wearer under the influence of both contractions.

In this way, the second standup portion 25 of the waist three-dimensional gather part 20 is prone to formation of a gap from the skin of the wearer, and its standup state changes characteristically depending on the size of the gap between the interior face of the product and the skin surface of the wearer, as shown in FIGS. 7 to 8 (a). Specifically, while the gap is smaller, the second standup portion 25 of the waist three-dimensional gather part 20 has its free edge oriented toward the waist edge, has a smaller standup angle, and is in surface contact, as shown in FIG. 7(a). That is, at a lower risk for leakage, excellent wearing feeling and fitting is ensured. On the other hand, while the gap is growing, the second standup portion 25 of the waist three-dimensional gather part 20 is raised higher in its free edge area as shown in FIG. 7(b), and is turned over (if not, raised higher up to a nearly turned-over state) toward the crotch side in its free edge area in the middle of the width direction WD as shown in FIGS. 8(a) and 9 when the constriction around the lower torso is particularly loosened. That is, at a higher risk for leakage, the second standup portion 25 changes its form to provide still more excellent leak protection. Such change in form of the waist three-dimensional gather part 20 has never been proposed to date, and effectively functions against back leakage or front leakage derived from loosening of the article in the worn state over time (e.g., at meal times or the like).

The second laid-down portions 24 in the illustrated embodiment are interposed between the top sheet 2 and the side three-dimensional sheet 4s in the first back laid-down portions 4e, and bonded therebetween with joining means, such as a hot melt adhesive, but may alternatively be disposed on the side three-dimensional sheet 4s in the first back laid-down portions 4e. In other words, the waist three-dimensional gather part 20 may be disposed on the side three-dimensional gather parts 4, though not shown.

The waist three-dimensional sheet 26 is not particularly limited in type, and is usually water-repelling for securing liquid-shielding property. In particular, for imparting both texture and liquid-shielding property, nonwoven fabric having at least one melt-blown layer between spunbonded layers (SMS nonwoven fabric, SMMS nonwoven fabric, SSMS nonwoven fabric, or SSMMS nonwoven fabric) is preferred. One sheet of nonwoven fabric may be used, or a plurality of sheets of nonwoven fabric may be stacked and used. In the latter case, the nonwoven sheets may preferably be adhered together with a hot melt adhesive or the like.

Each second three-dimensional elastic members 21 may be made of a material that is usually used, for example, natural rubber or synthetic rubber formed into, for example, a thread, string, or tape shape, specifically, polystyrene rubber, polyolefin rubber, polyurethane rubber, polyester rubber, polyurethane, polyethylene, polystyrene, styrene-butadiene copolymer, silicone, or polyester. A plurality of the second three-dimensional elastic members 21 may be arranged at intervals as in the illustrated embodiment, or only one of them may be disposed. The stretch rate of the second three-dimensional elastic members 21 in the spread state may suitably be decided, and may be, for example, about 130 to 250%, in particular about 160 to 200% in the case of spandex rubber threads having a fineness of about 600 to 1300 dtex.

When a plurality of the second three-dimensional elastic members 21 are provided at intervals in the front-back direction LD, all of the second three-dimensional elastic members 21 may have the same stretch rate, or some or all of them may have different stretch rates. For example, it is preferred that the second three-dimensional elastic members 21 have lower stretch rates in the spread state with increasing proximity to the waist edge, which facilitates turning over of the second standup portion 25 in its free edge area.

The position of the second three-dimensional elastic members 21 may suitably be decided, and the second three-dimensional elastic member 21 located in the free edge area (closest to the waist edge) is preferably positioned about 2 to 40 mm apart from the back edge of the waist root zone 22, so that the second standup portion 25 is more easily turned over in its free edge area. For the similar reason, the second three-dimensional elastic member 21 located in the free edge area (closest to the waist edge) is preferably positioned apart from the front edge of the end flap EF.

A tape-type disposable diaper is prone to formation of a gap between the skin and the area located on the waist edge side of the attaching parts 9 (where a plurality of attaching parts 9 are arranged in the front-back direction LD, the one located closest to the waist edge). Accordingly, the waist three-dimensional gather part 20 preferably has at least one second three-dimensional elastic member 21 located on the waist edge side of the attaching parts 9 in the spread state, so that the deformation of the waist three-dimensional gather part 20 as discussed above is effectively developed.

It is also preferred that, as in the embodiment shown in FIGS. 6 to 8, the waist three-dimensional gather part 20 has a third zone 33 extending from the waist root zone 22 toward the crotch section, third laid-down portions 34 formed by fixing the lateral end portions opposed in the width direction WD of the third zone 33 in a laid down state, a third standup portion 35 formed by unfixing a part of the third zone 33 between the third laid-down portions 34, and third three-dimensional elastic members 31 fixed at least to the free edge area of the third standup portion 35. In this way, the third zone 33 basically blocks the migration of the bodily waste, and the second zone 23 blocks leakage of the bodily waste which has somehow overflown the third zone 33, providing a two-stage leak protection function. Here, as the second zone 23 has the shielding function which is basically different from that of the third zone 33 as discussed above, the leak protection property is naturally more excellent than the case where the same standup portions are simply provided in duplicate.

It is indisputable that the third zone 33 may be omitted as in the embodiment shown in FIG. 10. Further, as in the embodiment shown in FIG. 8(b), a plurality of the second zones 23 may be arranged at intervals in the front-back direction LD.

In the illustrated embodiment, the third zone 33 of the waist three-dimensional gather part 33 is located in an extent in the front-back direction LD containing the first standup portions 4f of the side three-dimensional gather parts 4, but part or all of the third zone 33 may be located in an extent in the front-back direction LD containing the first laid-down portions. In the former case, each third laid-down portion 34 is brought to a region containing the corresponding side root zone 4x, whereas in the latter case, each third laid-down portion 34 may be placed in a region containing the corresponding first back laid-down portion 4e.

Further, when the third zone 33 of the waist three-dimensional gather part is located in an extent in the front-back direction LD containing the first standup portions 4*f* of the side three-dimensional gather parts 4, it is preferred that the third standup portion 35 and the first standup portions 4*f* are not joined where they overlap with each other, but may alternatively be joined.

In the embodiments discussed above, the waist three-dimensional gather part 20 is provided only in the dorsal section B, but may also be provided in the ventral section F in addition to this. That is, a waist three-dimensional gather part 20 may be provided at least one of between the first front laid-down portions 4*b* and between the first back laid-down portions 4*e*.

In the embodiments discussed above, the waist three-dimensional gather part 20 also acting as the deformable stretching/contracting member 50 is provided, but alternatively a dedicated deformable stretching/contracting member 50 without the shielding property may be provided. For example, in the illustrated embodiment, when the waist root zone 22 is omitted to leave only the second zone 23, the shielding property is lost, but the transverse portion 62 and the obliquely backward portions 63 may be formed in the natural length state. Further, it is preferred to provide the deformable stretching/contracting member 50 on the top face as in the embodiments discussed above, but the deformable stretching/contracting member 50 may alternatively be provided on the under face. The detailed structure other than these locational modifications are the same as for the waist three-dimensional gather part 20, so that further explanation is omitted.

<Nonwoven Fabric>

As the nonwoven fabric in the description hereinabove, commonly known nonwoven fabric may suitably be used depending on the parts or purposes. Examples of the constituent fibers of the nonwoven fabric include, but not limited to, synthetic fibers, such as polyolefin-based, e.g., polyethylene or polypropylene, polyester-based, or polyamide-based fibers (including not only single component fibers, but also composite fibers, such as of core/sheath type), as well as regenerated fibers, such as rayon or cupra, or natural fibers, such as cotton, and also mixtures thereof. For improved flexibility of the nonwoven fabric, the constituent fibers may preferably be crimped fibers. The constituent fibers of the nonwoven fabric may also be hydrophilic fibers (including those rendered hydrophilic with hydrophilizers), hydrophobic fibers, or water-repelling fibers (including those rendered water-repelling with water repellents). Further, nonwoven fabric may generally be categorized into discontinuous fiber nonwoven, continuous fiber nonwoven, spunbonded nonwoven, melt blown nonwoven, spunlace nonwoven, thermal bonded (air through) nonwoven, needle-punched nonwoven, point-bonded nonwoven, composite nonwoven (SMS or SMMS nonwoven fabric having a melt blown layer interposed between spunbonded layers), or the like nonwoven fabric, generally depending on the length of the fibers, method of forming the sheet, method of joining the fibers, or layered structure, and any of these nonwoven fabric may be used.

<Explanation of Terms in the Specification>

The following terms appearing in the present specification shall have the following means unless otherwise specified herein.

The "front-back direction" refers to the direction shown by the reference sign LD (longitudinal direction) in the figures, whereas the "width direction" refers to the direction shown by the reference sign WD (right-left direction) in the figures, and the front-back direction and the width direction are orthogonal to each other.

The "MD" and "CD" refer to the flow direction (MD: machine direction) and the lateral direction orthogonal thereto (CD: cross direction) in the production facilities, respectively, and either one of these is aligned to the front-back direction while the other is aligned to the width direction, depending on the parts of the product. The MD of nonwoven fabric is the direction of fiber orientation in the nonwoven fabric. The fiber orientation refers to the direction along which the fibers of the nonwoven fabric are aligned, and may be identified, for example, by a measurement method pursuant to the fiber orientation testing method using zero-span tensile strength prescribed in TAPPI Standard Method T481, or by a simplified measurement method for determining the fiber orientation by the ratio of tensile strengths in the front-back direction and in the width direction.

The "top side" refers to the side, when the article is worn, closer to the skin of the wearer, whereas the "underside" refers to the side, when the article is worn, away from the skin of the wearer.

The "top face" refers to the face, when the article is worn, closer to the skin of the wearer, whereas the "under face" refers to the face, when the article is worn, away from the skin of the wearer.

The "stretch rate" refers to a value with respect to the natural length being 100%. For example, a 200% stretch rate is synonymous with stretch in two folds.

The "gel strength" is determined as follows. To 49.0 g of artificial urine (a mixture of 2 wt % urea, 0.8 wt % sodium chloride, 0.03 wt % calcium chloride dihydrate, 0.08 wt % magnesium sulfate heptahydrate, and 97.09 wt % ion-exchanged water), 1.0 g of superabsorbent polymer is added and stirred with a stirrer. The resulting gel is left in a chamber with constant temperature and humidity at 40° C. at 60% RH for 3 hours, and then the temperature is returned to the ordinary temperature. The gel strength is measured in a curd meter (Curd-meter-MAX ME-500 manufactured by I. techno Engineering).

The "basis weight" is determined as follows. A specimen or test piece is preliminarily dried, left in a laboratory or in apparatus under the standard conditions (23±1° C. temperature and 50±2% relative humidity in the testing location) until constant mass is attained. The preliminary drying refers to attaining constant mass from a specimen or test piece in the environment at a temperature of 100° C. No preliminary drying may be performed on fibers with an official regain of 0.0%. From the test piece of the constant mass, a specimen of 100 mm×100 mm size is cut out using a sampling template (100 mm×100 mm). The weight of the specimen is measured and multiplied by 100 times to calculate the weight per 1 $m^2$, which is taken as the basis weight.

The "thickness" is automatically measured using an automatic thickness meter (KES-G5 handy compression tester program) under a load of 0.098 $N/cm^2$ with the compression area of 2 $cm^2$. The thickness of perforated nonwoven fabric is measured at a position other than the apertures and the protrusions therearound.

The water absorption is determined in accordance with JIS K7223-1996 "Testing method for water absorption capacity of super absorbent polymers".

The water absorption speed is defined as the "time spent until the end point is reached" in carrying out JIS K7224-1996 "Testing method for water absorption rate of super absorbent polymers" using 2 g of superabsorbent polymer and 50 g of saline.

The direction of fiber orientation in nonwoven fabric refers to the direction along which the fibers of the nonwoven fabric are aligned, and may be identified, for example, by a measurement method pursuant to the fiber orientation testing method using zero-span tensile strength prescribed in TAPPI Standard Method T481, or by a simplified measurement method for determining the fiber orientation by the ratio of tensile strengths in the front-back direction and in the width direction.

The "spread state" refers to the state in which an article is spread flatly without contraction (including any contraction, such as contraction by means of elastic members) or slack.

The size of each part refers to the size not in the natural length state but in the spread state, unless otherwise specified.

A test or measurement shall be, in the absence of description about environmental conditions, performed in a laboratory or in apparatus under the standard conditions (23±1° C. temperature and 50±2% relative humidity in the testing location).

INDUSTRIAL APPLICABILITY

The present invention is applicable to attachable-type disposable wearing articles, such as the tape-type disposable diapers as described above as examples.

DESCRIPTION OF REFERENCE SIGNS

1: liquid-impervious sheet
10: perforated line
12: exterior nonwoven sheet
2: top sheet
20: waist three-dimensional gather part
21: second three-dimensional elastic member
22: waist root zone
23: second zone
24: second laid-down portion
25: second standup portion
26: waist three-dimensional sheet
3: absorber body
31: third three-dimensional elastic member
33: third zone
34: third laid-down portion
35: third standup portion
4: side three-dimensional gather part
4b: first front laid-down portion
4G: first three-dimensional elastic member
4c: first zone
4e: first back laid-down portion
4f: first standup portion
4s: side three-dimensional sheet
4x: side root zone
5: attachable tape
50: deformable stretching/contracting member
51: fixed area
52: unfixed area
6: target sheet
60: side area
61: intermediate area
62: transverse portion
63: obliquely backward portion
71: first folding line
72: second folding line 80: easy-fold area
9: attaching part
B: dorsal section
EF: end flap
F: ventral section
LD: front-back direction
SF: side flap
WD: width direction
i: iliac crest

The invention claimed is:

1. An attachable-type disposable wearing article having:
a crotch section containing a center of front-back direction, a ventral section extending forward of the center of the front-back direction, and a dorsal section extending backward of the center of the front-back direction,
the attachable-type disposable wearing article comprising:
attaching parts provided in opposed lateral portions of the dorsal section, and to be detachably attached to an exterior face of the ventral section,
an absorber body disposed in a region including the crotch section,
an end flap exclusive of the absorber body located backward of the absorber body in the dorsal section, and
a deformable stretching/contracting member fixed to the end flap,
the deformable stretching/contracting member having a pair of fixed areas fixed in lateral portions, respectively, opposed in a width direction of the end flap, and an unfixed area elastically stretchable/contractible in the width direction and located between the fixed areas,
wherein the attachable-type disposable wearing article is configured so that, in a natural length state, as the unfixed area contracts, a pair of side areas of the end flap positioned lateral to the unfixed area are obliquely drawn closer to each other as they extend backward, which results in formation of obliquely backward portions at back edges of the side areas which are positioned more backward as they extend laterally, while a transverse portion extends in the width direction at a back edge of an intermediate area located between the pair of side areas are formed, and
in a spread state, a back edge of the end flap extends along the width direction over an extent including from one of the obliquely backward portions to the other, and
wherein the pair of fixed areas is positioned within an extent in the width direction corresponding to an entire width of the absorber body.

2. An attachable-type disposable wearing article according to claim 1, further comprising:
a pair of first folding lines linearly extending in the front-back direction and each passing a boundary between the unfixed area and one of the fixed areas,
a pair of second folding lines each extending along a bisector of an internal angle formed by a position of one of the first folding lines in a spread state and a position of the first folding line in a natural length state, wherein a fold is to be made along each second folding line in a direction opposite from a direction in which a fold is to be made along a corresponding first folding line, and
wherein an easy-fold area is formed along each second folding line.

3. The attachable-type disposable wearing article according to claim 1, further comprising:
a pair of first folding lines linearly extending in the front-back direction and each passing a boundary between the unfixed area and one of the fixed areas, a pair of second folding lines each extending along a bisector of an internal angle formed by a position of one of the first folding lines in a spread state and a position of the first folding line in a natural length state, wherein a fold is to be made along each second folding line in a direction opposite from a direction in which a fold is to be made along a corresponding first folding line, wherein vertices between the first folding lines and the second folding lines are located forward of a back edge of the absorber body, and wherein the absorber body is free of parts each present between one of the first folding lines and a corresponding second folding line in the spread state.

4. The attachable-type disposable wearing article according to claim 1, wherein a dimension in the width direction of an elastically stretchable/contractible zone in the unfixed area is 10 to 25% an overall length of the article, wherein a stretch rate of the unfixed area is 120 to 300%, and wherein a distance between the back edge of the absorber body and a front edge of an elastic material contained in the unfixed area is 0 to 10% the overall length of the article.

5. The attachable-type disposable wearing article according to claim 1, further comprising:

side three-dimensional gather parts standing up from a top face along first shielding positions on lateral sides opposed in the width direction, wherein each of the side three-dimensional gather parts has a side root zone fixed outward in the width direction of a first shielding position, and a first zone extending from the side root zone, and comprises a first front laid-down portion and a first back laid-down portion formed by fixing front and back end portions, respectively, of the first zone in a laid down state, a first standup portion formed by unfixing the first zone between the first front laid-down portion and the first back laid-down portion, and a first three-dimensional elastic member fixed at least to a free edge area of the first standup portion, wherein the first standup portion in at least its free edge area is contracted in the front-back direction together with the first three-dimensional elastic member and is stretchable in the front-back direction, the attachable-type disposable wearing article further comprising:

a waist three-dimensional gather part standing up from a top face along a second shielding position between the first back laid-down portions, wherein the waist three-dimensional gather part has a waist root zone fixed along the second shielding position and a second zone extending from the waist root zone toward a back edge, and comprises second laid-down portions formed by fixing lateral end portions opposed in the width direction of the second zone in a laid down state, a second standup portion formed by unfixing a part of the second zone between the second laid-down portions, and a second three-dimensional elastic member fixed at least to a free edge area of the second standup portion, wherein the second standup portion in at least its free edge area is contracted in the width direction together with the second three-dimensional elastic member and is stretchable in the width direction, wherein the deformable stretching/contracting member is the waist three-dimensional gather part, wherein the pair of fixed areas are the second laid-down portions, and wherein the unfixed area is the second standup portion.

6. The attachable-type disposable wearing article having:

a crotch section containing a center of front-back direction, a ventral section extending forward of the center of the front-back direction, and a dorsal section extending backward of the center of the front-back direction, the attachable-type disposable wearing article comprising:

attaching parts provided in opposed lateral portions of the dorsal section, and to be detachably attached to an exterior face of the ventral section, an absorber body disposed in a region including the crotch section, an end flap exclusive of the absorber body located backward of the absorber body in the dorsal section, and a deformable stretching/contracting member fixed to the end flap, the deformable stretching/contracting member having a pair of fixed areas fixed in lateral portions, respectively, opposed in a width direction of the end flap, and an unfixed area elastically stretchable/contractible in the width direction and located between the fixed areas, wherein the attachable-type disposable wearing article is configured so that, in a natural length state, as the unfixed area contracts, a pair of side areas of the end flap positioned lateral to the unfixed area are obliquely drawn closer to each other as they extend backward, which results in formation of obliquely backward portions at back edges of the side areas which are positioned more backward as they extend laterally, while a transverse portion extends in the width direction at a back edge of an intermediate area located between the pair of side areas are formed, and in a spread state, a back edge of the end flap extends along the width direction over an extent including from one of the obliquely backward portions to the other, and the attachable-type disposable wearing article further comprising:

a pair of first folding lines linearly extending in the front-back direction and each passing a boundary between the unfixed area and one of the fixed areas, a pair of second folding lines each extending along a bisector of an internal angle formed by a position of one of the first folding lines in a spread state and a position of the first folding line in a natural length state, wherein a fold is to be made along each second folding line in a direction opposite from a direction in which a fold is to be made along a corresponding first folding line, and wherein an easy-fold area is formed along each second folding line.

7. The attachable-type disposable wearing article according to claim 6, further comprising:

a pair of first folding lines linearly extending in the front-back direction and each passing a boundary between the unfixed area and one of the fixed areas, a pair of second folding lines each extending along a bisector of an internal angle formed by a position of one of the first folding lines in a spread state and a position of the first folding line in a natural length state, wherein a fold is to be made along each second folding line in a direction opposite from a direction in which a fold is to be made along a corresponding first folding line, wherein vertices between the first folding lines and the second folding lines are located forward of a back edge of the absorber body, and wherein the absorber body is free of parts each present between one of the first folding lines and a corresponding second folding line in the spread state.

8. The attachable-type disposable wearing article according to claim 6, wherein a dimension in the width direction of an elastically stretchable/contractible zone in the unfixed area is 10 to 25% an overall length of the article, wherein a stretch rate of the unfixed area is 120 to 300%, and wherein a distance between the back edge of the absorber body and a front edge of an elastic material contained in the unfixed area is 0 to 10% the overall length of the article.

9. The attachable-type disposable wearing article according to claim 6, further comprising:

side three-dimensional gather parts standing up from a top face along first shielding positions on lateral sides opposed in the width direction, wherein each of the side three-dimensional gather parts has a side root zone fixed outward in the width direction of a first shielding position, and a first zone extending from the side root zone, and comprises a first front laid-down portion and a first back laid-down portion formed by fixing front and back end portions, respectively, of the first zone in a laid down state, a first standup portion formed by unfixing the first zone between the first front laid-down portion and the first back laid-down portion, and a first three-dimensional elastic member fixed at least to a free edge area of the first standup portion, wherein the first standup portion in at least its free edge area is contracted in the front-back direction together with the first three-dimensional elastic member and is stretchable in the front-back direction, the attachable-type disposable wearing article further comprising:

a waist three-dimensional gather part standing up from a top face along a second shielding position between the first back laid-down portions, wherein the waist three-dimensional gather part has a waist root zone fixed along the second shielding position and a second zone extending from the waist root zone toward a back edge, and comprises second laid-down portions formed by fixing lateral end portions opposed in the width direction of the second zone in a laid down state, a second standup portion formed by unfixing a part of the second zone between the second laid-down portions, and a second three-dimensional elastic member fixed at least to a free edge area of the second standup portion, wherein the second standup portion in at least its free edge area is contracted in the width direction together with the second three-dimensional elastic member and is stretchable in the width direction, wherein the deformable stretching/contracting member is the waist three-dimensional gather part, wherein the pair of fixed areas are the second laid-down portions, and wherein the unfixed area is the second standup portion.

10. An attachable-type disposable wearing article having:

a crotch section containing a center of front-back direction, a ventral section extending forward of the center of the front-back direction, and a dorsal section extending backward of the center of the front-back direction, the attachable-type disposable wearing article comprising:

attaching parts provided in opposed lateral portions of the dorsal section, and to be detachably attached to an exterior face of the ventral section, an absorber body disposed in a region including the crotch section, an end flap exclusive of the absorber body located backward of the absorber body in the dorsal section, and a deformable stretching/contracting member fixed to the end flap, the deformable stretching/contracting member having a pair of fixed areas fixed in lateral portions, respectively, opposed in a width direction of the end flap, and an unfixed area elastically stretchable/contractible in the width direction and located between the fixed areas, wherein the attachable-type disposable wearing article is configured so that, in a natural length state, as the unfixed area contracts, a pair of side areas of the end flap positioned lateral to the unfixed area are obliquely drawn closer to each other as they extend backward, which results in formation of obliquely backward portions at back edges of the side areas which are positioned more backward as they extend laterally, while a transverse portion extends in the width direction at a back edge of an intermediate area located between the pair of side areas are formed, and in a spread state, a back edge of the end flap extends along the width direction over an extent including from one of the obliquely backward portions to the other, and the attachable-type disposable wearing article further comprising:

a pair of first folding lines linearly extending in the front-back direction and each passing a boundary between the unfixed area and one of the fixed areas, a pair of second folding lines each extending along a bisector of an internal angle formed by a position of one of the first folding lines in a spread state and a position of the first folding line in a natural length state, wherein a fold is to be made along each second folding line in a direction opposite from a direction in which a fold is to be made along a corresponding first folding line, wherein vertices between the first folding lines and the second folding lines are located forward of a back edge of the absorber body, and wherein the absorber body is free of parts each present between one of the first folding lines and a corresponding second folding line in the spread state.

11. The attachable-type disposable wearing article according to claim 10, wherein a dimension in the width direction of an elastically stretchable/contractible zone in the unfixed area is 10 to 25% an overall length of the article, wherein a stretch rate of the unfixed area is 120 to 300%, and wherein a distance between the back edge of the absorber body and a front edge of an elastic material contained in the unfixed area is 0 to 10% the overall length of the article.

12. The attachable-type disposable wearing article according to claim 10, further comprising:

side three-dimensional gather parts standing up from a top face along first shielding positions on lateral sides opposed in the width direction, wherein each of the side three-dimensional gather parts has a side root zone fixed outward in the width direction of a first shielding position, and a first zone extending from the side root zone, and comprises a first front laid-down portion and a first back laid-down portion formed by fixing front and back end portions, respectively, of the first zone in a laid down state, a first standup portion formed by unfixing the first zone between the first front laid-down portion and the first back laid-down portion, and a first three-dimensional elastic member fixed at least to a free edge area of the first standup portion, wherein the first standup portion in at least its free edge area is contracted in the front-back direction together with the first three-dimensional elastic member and is stretchable in the front-back direction, the attachable-type disposable wearing article further comprising:

a waist three-dimensional gather part standing up from a top face along a second shielding position between the first back laid-down portions, wherein the waist three-dimensional gather part has a waist root zone fixed along the second shielding position and a second zone extending from the waist root zone toward a back edge, and comprises second laid-down portions formed by fixing lateral end portions opposed in the width direction of the second zone in a laid down state, a second standup portion formed by unfixing a part of the second zone between the second laid-down portions, and a second three-dimensional elastic member fixed at least to a free edge area of the second standup portion, wherein the second standup portion in at least its free edge area is contracted in the width direction together with the second three-dimensional elastic member and is stretchable in the width direction, wherein the deformable stretching/contracting member is the waist three-dimensional gather part, wherein the pair of fixed areas are the second laid-down portions, and wherein the unfixed area is the second standup portion.

* * * * *